United States Patent [19]

Hedengren

[11] Patent Number: 5,371,461
[45] Date of Patent: Dec. 6, 1994

[54] APPARATUS AND METHOD FOR COMPENSATING FOR VARIATIONS IN THE LIFT-OFF OF EDDY CURRENT SURFACE INSPECTION ARRAY ELEMENTS

[75] Inventor: Kristina H. V. Hedengren, Schenectady, N.Y.

[73] Assignee: General Electric Company, Schenectady, N.Y.

[21] Appl. No.: 32,369

[22] Filed: Mar. 17, 1993

Related U.S. Application Data

[63] Continuation-in-part of Ser. No. 904,634, Jun. 26, 1992, abandoned.

[51] Int. Cl.⁵ .................... G01N 27/90; G01R 33/12
[52] U.S. Cl. .................... 324/225; 324/240; 324/241; 324/242; 324/262
[58] Field of Search ........ 324/202, 225, 232, 238–243, 324/262

[56] References Cited

U.S. PATENT DOCUMENTS

| | | | |
|---|---|---|---|
| 4,528,506 | 7/1985 | Davis et al. | 324/225 |
| 4,608,534 | 8/1986 | Cecco et al. | 324/238 |
| 4,661,777 | 4/1987 | Tornblom | 324/225 |
| 4,686,471 | 8/1987 | Morita et al. | 324/243 |
| 4,703,265 | 10/1987 | Tornblom | 324/225 X |
| 4,808,927 | 2/1989 | Cecco et al. | 324/225 X |
| 4,843,318 | 6/1989 | Greenblatt et al. | 324/225 |
| 4,851,774 | 7/1989 | Tornblom | 324/225 |
| 5,047,719 | 9/1991 | Johnson et al. | 324/242 |
| 5,130,651 | 7/1992 | Morrey, Jr. | 324/225 |
| 5,182,513 | 1/1993 | Young et al. | 324/232 |
| 5,184,070 | 2/1993 | Besendorfer et al. | 324/225 |
| 5,262,722 | 11/1993 | Hedengren et al. | 324/242 |

Primary Examiner—Gerard R. Strecker
Attorney, Agent, or Firm—David C. Goldman; Paul R. Webb, II

[57] ABSTRACT

An improved eddy current probe array having means to compensate the entire array for varying different element liftoff, is described. An array consisting of a plurality of sense elements and means for compensating these sense elements is scanned across an inspection surface to produce respective scan responsive signals wherein the scan responsive signals of the sense elements are proportionately normalized or calibrated against the scan response of said compensating means during routine signal processing of the array signals in order to compensate for any lift off experienced by the sense elements. Array lift off compensation is attributable to sense element design cooperating with at least one lift off compensating sense element and a method of normalization/calibration performed during signal processing of the array signals.

20 Claims, 5 Drawing Sheets

APPARATUS AND METHOD FOR COMPENSATING FOR VARIATIONS IN THE LIFT-OFF OF EDDY CURRENT SURFACE INSPECTION ARRAY ELEMENTS

CROSS REFERENCE TO RELATED APPLICATIONS

This application is a continuation-in-part of application Ser. No. 07/904,634, filed Jun. 26, 1992, now abandoned.

FIELD OF THE INVENTION

This invention relates generally to eddy current inspection of an electrically conductive part using a surface scanning array and more particularly to an improved eddy current sense element array which enables compensation for lift off of sense elements caused by non-uniform element to surface spacing.

BACKGROUND OF THE INVENTION

Undesirable signals arise during routine eddy current inspection due to variations in separation distance between eddy current sense elements and the underlying inspection surface of a conductive part undergoing inspection. The term "lift off" is a term in the art that refers to the separation distance between sense element and inspection surface. Lift off signals are non-uniform among sense elements of an array whenever the array cannot maintain substantially the same separation between each element and the underlying inspection surface. Lift off contributions are capable of corrupting actual sense element measurement signals, thereby distorting or concealing signals otherwise due to near surface flaws and cracks. Thus, near surface flaw detection is impaired by lift off effects caused by unequal element to surface separation.

Typically, lift off signals are either suppressed or compensated for in a computational manner using signal processing techniques. The compensation method of U.S. Pat. No. 4,661,777 by Tornblom describes typical electronic signal processing on signals of multiple frequencies as a technique of compensation for aberrant lift off signals. U.S. Patent Nos. 4,808,927 by Cecco et al and 4,608,534 by Cecco et al utilize signal phase segregation rather than signal compensation to discriminate aberrant signals due to structural variations from actual measurement signals. Alternatively, a sense element itself can be optimized to be operated in such a way as to suppress or compensate for lift off effects by utilizing sufficiently dissimilar frequencies to generate different current penetration depths. A sense element design is selected to cooperate with the method of suppression and/or compensation providing an interdependent system like that described in U.S. Pat. No. 4,703,265 by Tornblom wherein such a sense element design is described. The sense element therein is designed in such a way that a complete or partial suppression of undesired lift off signal effect is achieved. This is accomplished utilizing a difference in depth of penetration for current induced in the conductive part at different carrier frequencies. Compensation or suppression by this sort of sense element design involves automatically adapting the use of dual excitation frequencies to optimize sense element response to inspection surface structure, thereby adjusting signal to noise ratio to a given type, shape and/or position of sense element. The effects of the difference between depth of current penetration into the inspection part at different frequencies can then be compensated for. A common multi-frequency inspection technique consists of recording data from at least two judiciously chosen, simultaneous frequencies then performing simultaneous frequency mixing in order to blank an unwanted signal that may be due to lift off.

Eddy current arrays have been used to speed up inspection scanning for near surface detection of flaws. However, surface irregularities encountered in array scanning the conductive part under inspection provide array sense element responses which include aberrant signal components contributing to non-uniformity among array sense element signals. This phenomenon jeopardizes the reliable use of arrays in production inspections as their ability to reliably detect near surface defects or flaws in the part is diminished.

It would therefore be desirable to design an eddy current array having means for compensating for aberrant lift off signals experienced by individual array elements. The array should be suitable for use in a production inspection environment.

SUMMARY

The invention is directed to an eddy current inspection array having a spatially correlated plurality of sense elements disposed therein; lift off compensating means disposed therein to cooperate with adaptively designed sense elements; drive means for coupling sense elements and lift off compensating means to a source of alternating current; means for array scanning the inspection surface in order to acquire discrete scan responsive signals from the sense elements and lift off compensating means; and means for processing these signals in order to proportionately normalize sense element signals with respect to that of the lift off compensating means thereby compensating for lift off.

An embodiment of a lift off compensating array includes a multi-layer array structure having at least one integrally disposed lift off compensating sense element organized in absolute configuration cooperating with a plurality of array sense elements organized in differential configuration in order to normalize and/or calibrate scan responsive array signals to lift off.

The invention is further directed to a lift off compensating method for inspection surface array scanning including the following steps: disposing a lift off compensating eddy current inspection array against an inspection surface of a conductive part, the array having a plurality of sense elements with means disposed therein to compensate for lift off, so as to mutually space the sense elements and lift off compensating means a respective mutually spaced apart distance from the inspection surface; mutually coupling the sense elements and lift off compensating means through the inspection surface to at least one drive element; array scanning the inspection surface to provide discrete scan responsive signals from the sense elements and lift off compensating means; and proportionately compensating each sense element signal to a uniform spaced apart distance based on the lift off compensating means signal and each comparative mutual spacing distance. Such processing, collectively normalizes the entire array response to a uniform spaced apart distance from the inspection surface. Furthermore, this uniform normalization distance can be calibrated to a predetermined value suitable for array threshold detection.

OBJECTS OF THE INVENTION

It is an object of the invention to provide a lift off compensating eddy current probe array design for reliable, efficient inspection in a production environment.

It is another object of the invention to use lift off experienced by at least one sense element to normalize and/or calibrate an entire array of elements.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

DETAILED DESCRIPTION OF THE INVENTION

Figure 1:
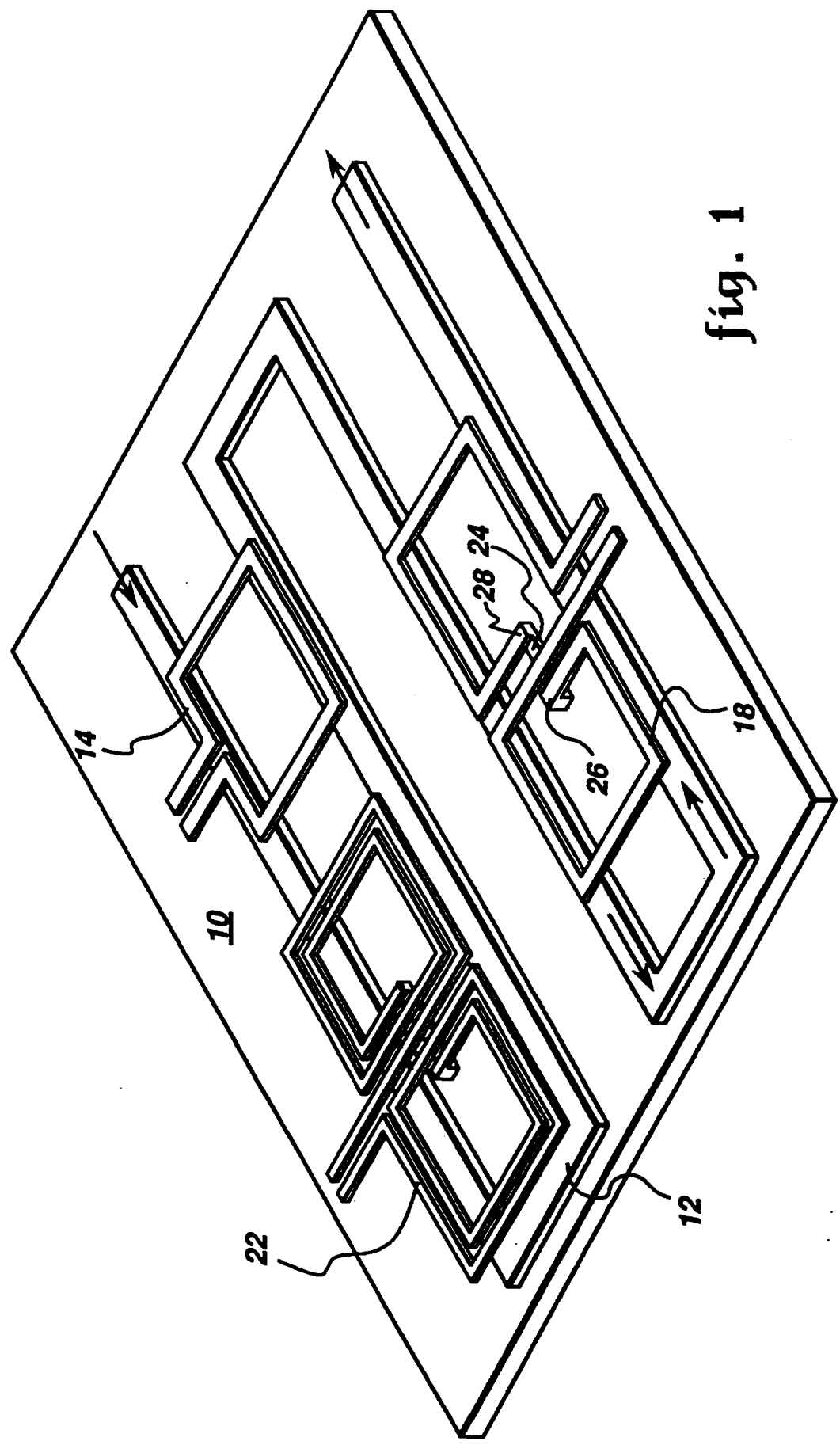
FIG. 1 is a schematic top perspective view illustrating a typical multi-layer eddy current array structure having three typical sense element configurations.

FIG. 1 illustrates an eddy current probe array structure having three illustrative sense elements disposed in multiple layers of flexible substrate. FIG. 1 shows a probe array structure 10 having a single serpentine drive element 12 disposed in a single layer underlying at least another layer wherein various sense elements are disposed. The direction of instantaneous current flow in drive element 12 is indicated by arrows as excited by an external source of alternating current (not shown). Three illustrative configurations for sense element design therein include: a single turn, single loop provides an absolute configuration 14, a single turn, double loop in differential configuration 18 and a double turn, double loop in differential configuration 22. The size, shape, location, number of layers, number of turns, number of loops, etc. can be varied to design an array for a particular inspection application. Sense elements, e.g. 14, 18, 22, are disposed so as to mutually couple to drive element 12 through an underlying inspection surface of a conductive part (not shown) in order to inspect for flaws by surface array scanning. Sense elements are generally characterized by multiple turns organized and connected in various configurations. Sense elements 18 and 22 illustrate a preferred sense element design having at least one turn per loop organized into double loops which are connected through a double layer structure in differential mode having a short segment 24 disposed in a layer other than that layer in which turns of each sense coil loop reside. When both coil elements or loops are organized to be substantially identical, connection 24 provides a 'virtual ground' operating as a common reference potential having nearly identical induced coil voltages. Thus signal cancellation advantages are provided by this type of sense element design wherein partial compensation is directly attributable to sense element design itself thereby suggesting its use in the preferred embodiment of this invention. Interlayer current conducting connections known as 'via' connections at 26 and 28 divert current conduction through the two coils of sense element 18 to another layer using conductive segment 24 thereby preserving a differential configuration yet avoiding any danger of electrically shorting the sense element. Sense elements 18 and 22 respectively illustrate single loop and double loop coils deposited substantially in the same layer. The illustrative drive and/or sense element configurations of FIG. 1 are only representative and not intended to exclude other single layer or multi-layer structures, having single or multiple loop coils connected in differential or absolute mode to operate in reflectance or bridge impedance configuration; or any other drive and/or sense element design within the scope of the invention. The configurations of FIG. 1 are presented merely to illustrate, in a simple manner, an extensive range of typical array element designs potentially available for use in various lift off compensating eddy current array designs.

A preferred embodiment of the present invention employs a multi-layer eddy current array having a plurality of substantially identical differential type sense elements disposed within a preferably flexible substrate.

Figure 2:
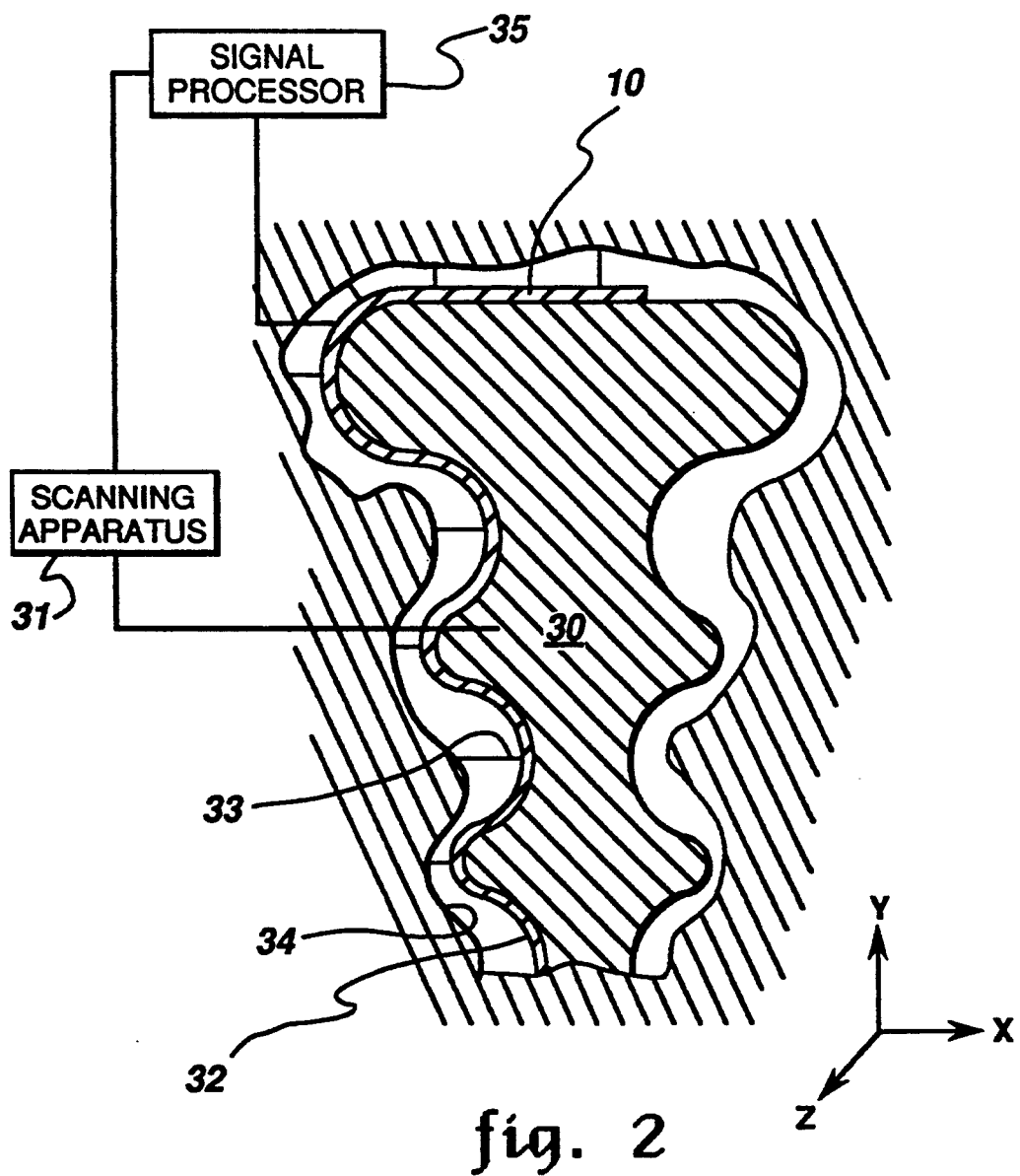
FIG. 2 is a cross sectional view through a slideably mounted array scanner having a scan conforming inspection surface onto which a flexible eddy current array of the type shown in FIG. 1 is surface mounted for illustrating respective nonuniform sense element to inspection surface spacing constituting lift off variation among scan responsive array sense elements.

FIG. 2 illustrates in cross section a mechanical array probe 30 mounted onto a conventional slideable scanning apparatus 31. Apparatus 31, preferably, is the slideable scanning/driving apparatus employed in commonly assigned U.S. Pat. No. 5,182,513 ('513), entitled "Method and Apparatus for Multi-channel, Multi-Frequency Data Acquisition System for Nondestructive Eddy Current Inspection Testing" to Young et al. A signal processor and scan controller 35 is operatively connected to scanning apparatus 31 and probe 30 by a commercially available connector such as the Fujipoly TM W series pressure deformable elastomeric connector. Scanning apparatus 31 and processor 35, preferably, are the same scanning apparatus and processor that are set forth to the above-identified '513 patent. A surface conforming eddy current array 10, herein flexible, is affixed to the surface of array probe 30 in an aligned and registered manner for surface scanning in a preferred direction herein normal to the page of the FIG. 2 along line Z. The array probe surface shape is a substantially matched and oppositely sized surface with respect to inspection surface 34. The array probe herein exhibits translational symmetry along the Z-axis. Inspection is therefore preferably accomplished by a single axial translation of array probe 30 along inspection surface 34 wherein array sense elements are sufficiently distributed to provide complete scanning coverage of inspection surface 34 in the preferred scan direction. As a practical matter, during routine inspection array scanning, mutual spacing distance 33 between sense elements of substantially conforming array surface 32 and part inspection surface 34 exhibit unavoidable non-uniformity due to imperfect fit. Respective non-uniformity in sense element to inspection surface separation is due to surface variations or an inability to achieve a close surface conforming fit during scanning, either of which contribute to mis-match among respective mutual surface separation distances of array sense elements. Non-uniform element to surface spacing from whatever source contributes to a lift off aberration associated with each array sense element signal.

Figure 3:
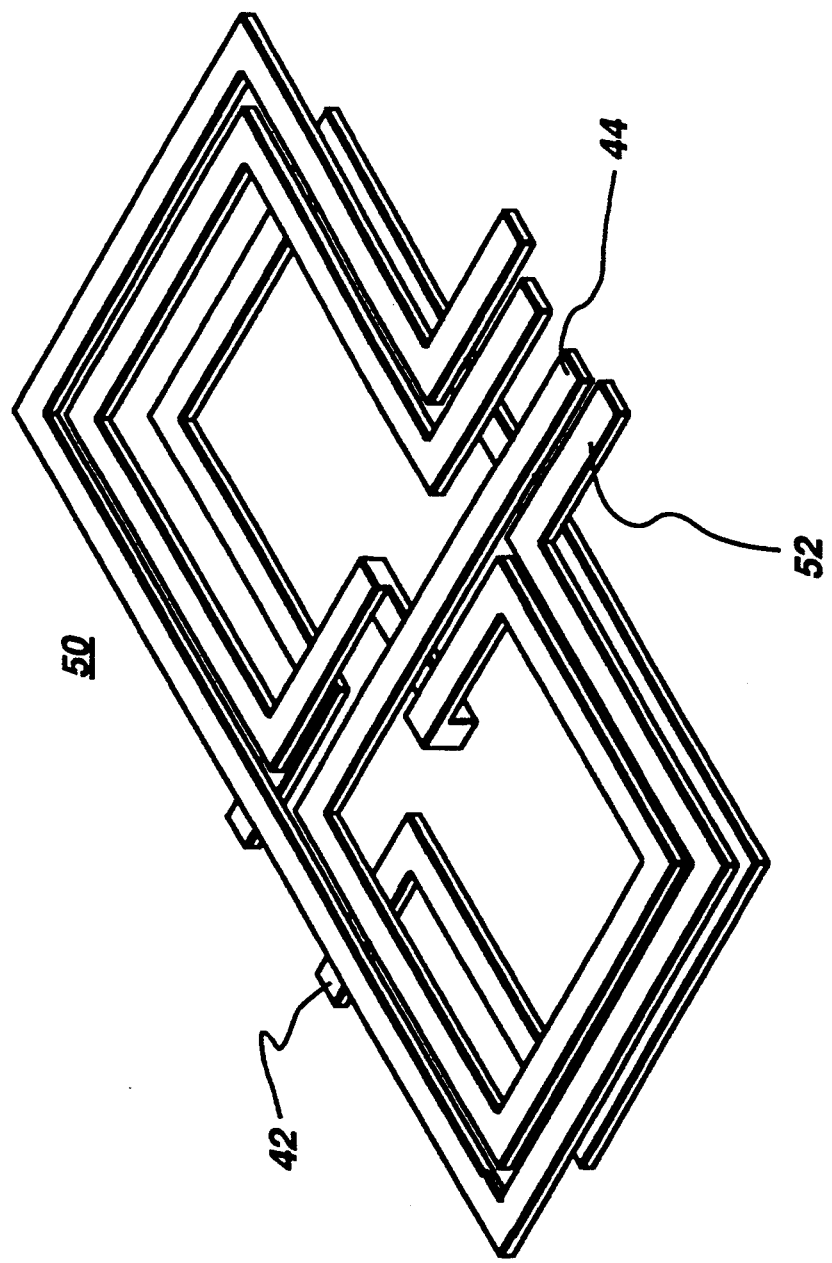
FIG. 3 is a schematic top perspective view of a single turn, single layer absolute drive element disposed in one layer; and in another layer, a single turn, single layer, absolute, lift off compensating sense element cooperating with a double turn, double layer differential sense element; these two sense elements being configured to cooperate as an element of a lift off compensating array having a plurality of such elements in accordance with the invention.

FIG. 3 illustrates one embodiment of a lift off compensating array element, e.g. 50, providing one element of a spatially correlated plurality of similar elements which comprise a lift off compensating array. Herein lift off compensating array element 50 consists of a sense element 44 cooperating with a lift off compensating means 52 in accordance with the invention. FIG. 3 shows a single turn, double loop, sense element in differential configuration, similar to the type described in FIG. 1 at 18, having a lift off compensation element 52 organized as a single layer, single turn sense element in absolute configuration, integrally fabricated, and proximally disposed in the same layer as sense element 44 to cooperate therewith. An operatively associated drive element 42 is herein disposed in a different layer. In operation sense element 44 and lift off compensating element 52 are excited by at least one drive element e.g. 42 wherein drive element 42 is interconnected to a source of alternating current (not shown) capable of at least one frequency of oscillation. Elements 42, 44 and 52 cooperate to provide a two layer lift off compensating array element 50. In accordance with the D invention, lift off compensating array element 52 operatively cooperates with associated sense elements, e.g. 44, to provide sense element signals which are proportionately normalized to the same mutual spacing distance between each sense element e.g. 44 and the inspection surface thereunder (not shown). In accordance with the invention, lift off compensation of the array is in part due to the differential configuration of sense elements cooperating with at least one, lift off compensating array sense element as discussed with reference to FIG. 3 and in part due to a method of normalization performed during signal processing through the use of processor 35 of each array sense element signal.

Figure 4:
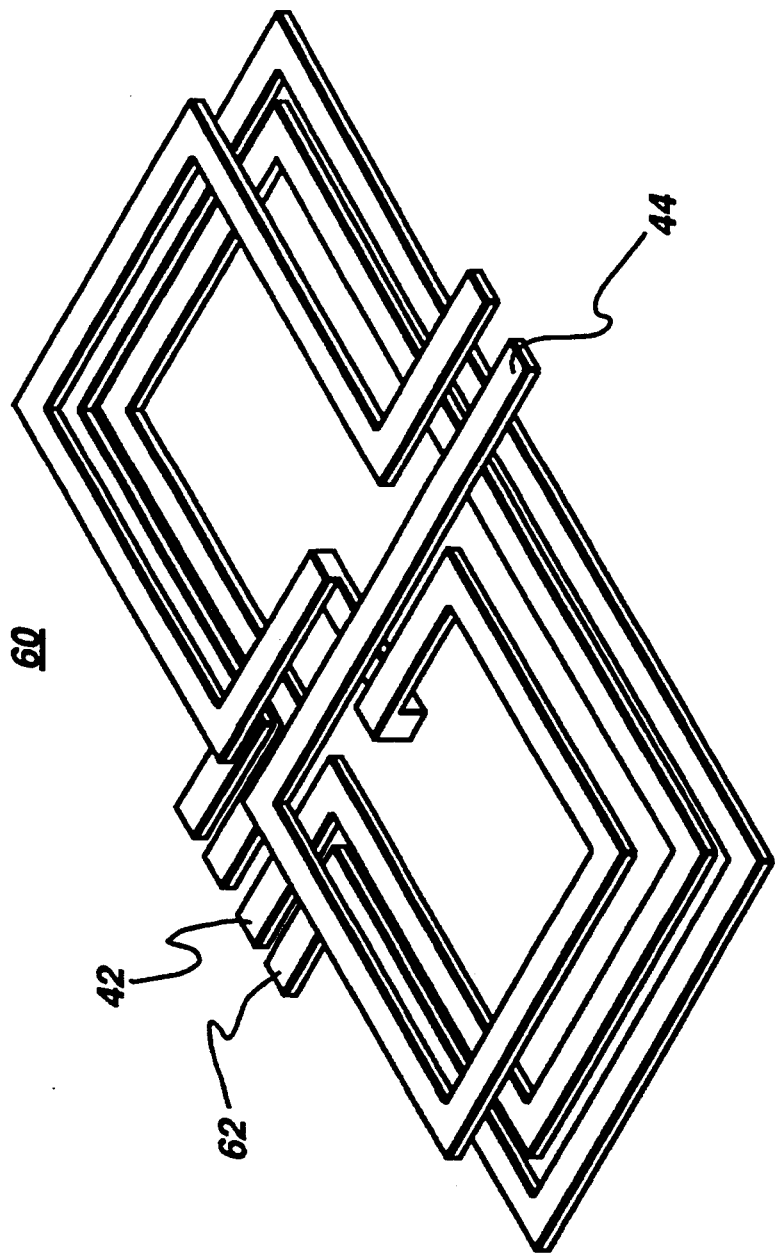
FIG. 4 is a schematic top perspective view of a single turn, single layer, absolute drive element and a single turn, single layer, absolute, lift off compensating sense element both disposed in the same layer; and a cooperating double turn, double layer differential sense element disposed substantially in another layer; the two sense elements being configured to cooperate as an element of a lift off compensating array having a plurality of such elements in accordance with the invention.

FIG. 4 illustrates another embodiment of a lift off compensating array element, e.g. 60, again providing one element of a spatially correlated plurality of similar elements comprising a lift off compensating array. Array element 60 has a sense element 44 design similar to that described in FIG. 3 being a single turn, double loop, sense element in differential configuration wherein an associated lift off compensating element 62 is organized as a single layer, single turn sense element in absolute configuration integrally fabricated and proximally disposed in the same layer as drive element 42. Sense coil 44 is disposed in a different layer therefrom. Lift off compensating sense element 62 and sense element 44 are operatively excited by at least one drive element e.g. 42. In accordance with the invention, array element design 60 is similarly interconnected but disposed in different layers than array element 50 described in FIG. 3. Elements 42, 44 and 62 operatively cooperate in a similar manner to provide an integral, lift off compensating, two layer array element 60 having similar array compensating features in accordance with the invention.

Figure 5A:
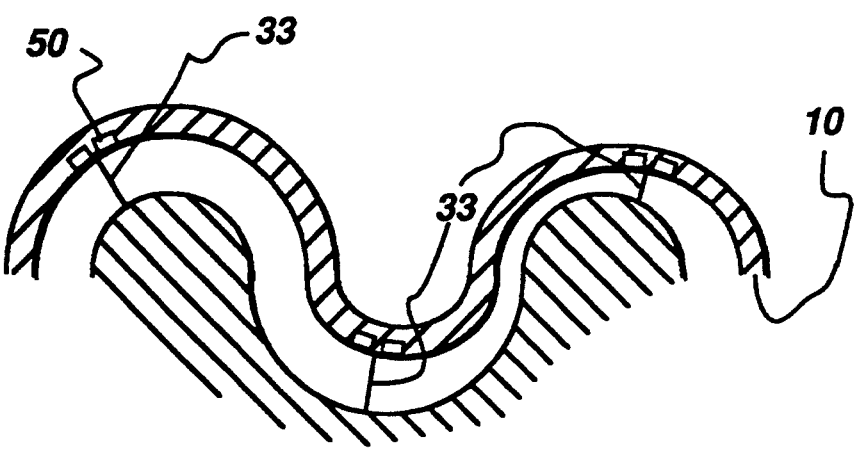
FIGS. 5a–5c schematically illustrates in accordance with the invention a method for utilizing a lift off compensating array to provide sense element by sense element normalization to a uniform array surface spacing separation; and further array calibration of this uniform array spacing separation to a predetermined value.
Figure 5B:
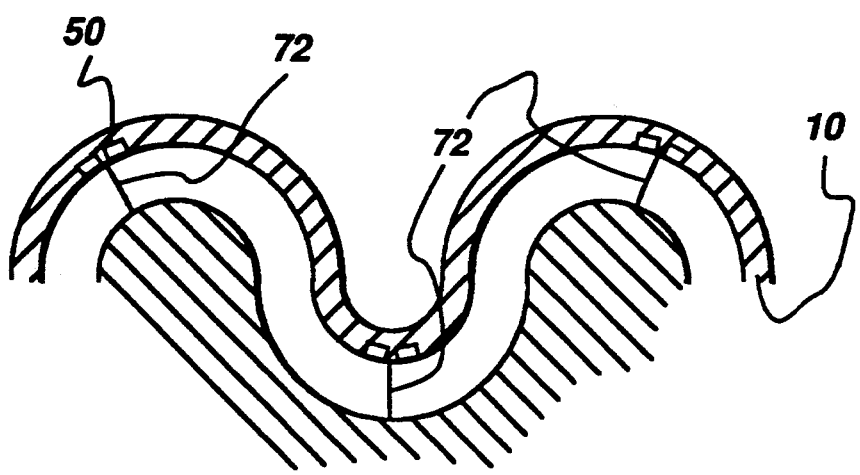
Figure 5C:
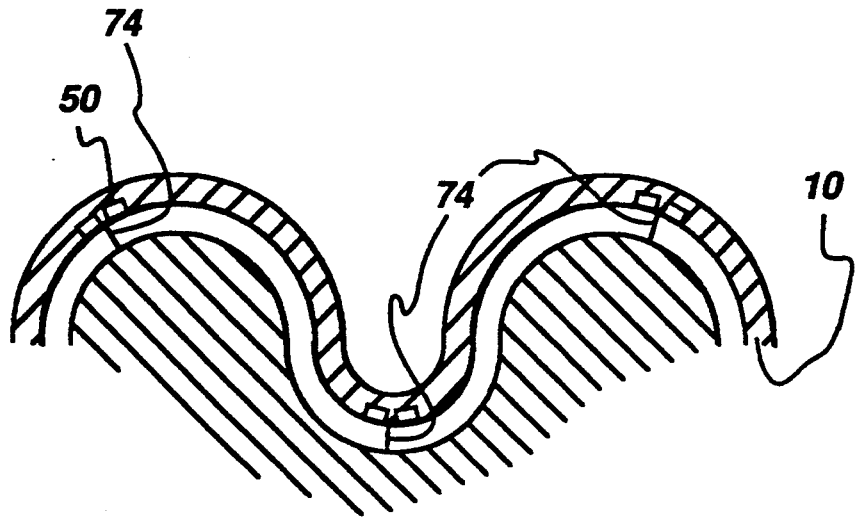

FIGS. 5a–5c illustrate a method of lift off compensation for an array. Array lift off compensation is accomplished in accordance with either of two embodiments of the method. As illustrated in FIG. 5a, mutual separation distances e.g. 33 of array elements e.g. 50 of array 10 exhibit non-uniform element to surface spacing. In FIG. 3 it was shown that sense element 44 cooperates with lift off compensating sense element 52 to comprise lift off compensating array element 50. In FIG. 5a, each respective non-uniform spacing e.g. 33 is proportionately normalized during signal processing through the use of processor 35 to the response of at least one lift off compensating sense element e.g. 52 (as shown in FIG. 3) for each sense element e.g. 44 (as shown in FIG. 3) in an element by element manner. This provides a uniform mutually spaced apart distance 72 for each array sense element wherein this separation distance as illustrated in FIG. 5b is not a predetermined value. FIG. 5c illustrates that the entire normalized array can be further calibrated to a particular predetermined mutual spaced apart distance 74 in a collective, rather than element by element, manner using at least one lift off compensating signal. This collective calibration approach is especially well suited to accommodating threshold detection inspection situations.

Lift off compensating elements need not be integrally nor proximately disposed with respect to sense elements of the array in order to cooperate therewith. This situation has only served as an illustrative example herein. Furthermore, lift off compensating sense elements need not have the same configuration as array sense elements nor the same drive source. Such has been presented herein only in the interest of simplicity for the purpose of illustration and explanation.

While specific embodiments of the invention have been illustrated and described herein, it is realized that numerous modifications and changes will occur to those skilled in the art. It is therefore understood that the appended claims are intended to cover all modifications and changes as fall within the true spirit and scope of the invention.

What is claimed is:

1. A lift off compensating eddy current inspection array apparatus comprising:
   a spatially correlated plurality of eddy current sense elements disposed within an array structure;
   lift-off compensating means disposed within said array structure for compensating said sense elements to lift-off;
   drive means for coupling said sense elements and said lift off compensating means to an external source of alternating current;
   means for array scanning in order to acquire discrete scan responsive signals from said sense elements and said lift off compensating means; and
   means for processing said discrete scan responsive signals in order to proportionately compensate said sense element signals with respect to said compensating means signal, said processing means normalizing said sense element signals to said compensating means signal.

2. An apparatus according to claim 1 wherein said drive means further comprises at least one drive element disposed within said array structure being interconnected to at least one external alternating current source.

3. An apparatus according to claim 2 wherein said sense elements and said array lift off compensating means cooperate with respect to one another to limit lift off distortion of said sense element signals.

4. An apparatus according to claim 3 wherein said sense elements and said array lift off compensating means are proximately disposed with respect to one another.

5. An apparatus in accordance with claim 2 wherein said array structure is flexible.

6. An apparatus in accordance with claim 2 wherein said drive and sense elements and said lift off compensating means are disposed in at least one layer of a multilayer structure.

7. An apparatus in accordance with claim 6 wherein said multilayer structure is further comprised of at least one layer of flexible substrate.

8. An apparatus in accordance with claim 6 wherein said at least one drive element is disposed onto at least one said layer.

9. An apparatus in accordance with claim 6 wherein said sense elements are selectively comprised of at least one coil deposited onto at least one said layer.

10. An apparatus in accordance with claim 9 wherein at least one said sense element is electrically interconnected in absolute mode.

11. An apparatus in accordance with claim 9 wherein said sense elements are selectively comprised of a plurality of electrically interconnected coils.

12. An apparatus in accordance with claim 11 wherein said sense elements are comprised of at least two coils electrically interconnected in differential mode.

13. An apparatus in accordance with claim 9 wherein said means for compensating for lift off further comprise at least one coil electrically interconnected in absolute mode.

14. An apparatus in accordance with claim 9 wherein said sense elements are configured in reflectance mode with at least one drive element.

15. An apparatus in accordance with claim 9 wherein said sense elements are configured in bridge impedance mode.

16. A lift off compensating method for surface array scanning to inspect an electrically conductive part for near surface flaws comprising:
 disposing an array against an inspection surface of said part, said array providing eddy current sense elements and at least one means for lift off compensating said sense elements;
 mutually coupling said sense elements and said lift off compensating means through said inspection surface to an external source of alternating current by at least one drive element;
 scanning said inspection surface with said array in order to provide discrete scan responsive signals from said sense elements and said lift off compensating means respectively; and
 compensating said scan responsive sense element signals for respective variation in mutually spaced apart distances between said sense elements and said inspection surface by proportionately normalizing said signals to lift off compensating means signal.

17. Method according to claim 16 wherein said step of compensating further includes comparing by proportionately normalizing each said sense element signal with respect to a uniform spaced apart distance.

18. Method according to claim 16 wherein said step of compensating further includes comparing by proportionately calibrating each said signal with respect to a predetermined spaced apart distance.

19. Method according to claim 17 wherein said step of compensating further includes comparing by proportionately calibrating each said signal with respect to a predetermined spaced apart distance.

20. Method according to claim 16 wherein said step of disposing further includes comfortably affixing said array to a slideable mechanical scanner said scanner having a surface which is substantially an oppositely signed, matched complement of said inspection surface for performing array scanning in a preferred direction.

* * * * *